US009716371B2

(12) United States Patent
 Burrows

(10) Patent No.: US 9,716,371 B2
(45) Date of Patent: Jul. 25, 2017

(54) NON-INVASIVE METHOD FOR RESONANT FREQUENCY DETECTION IN CORONA IGNITION SYSTEMS

(71) Applicant: Federal-Mogul Ignition Company, Southfield, MI (US)

(72) Inventor: John Antony Burrows, Timperly (GB)

(73) Assignee: FEDERAL-MOGUL IGNITION COMPANY, Southfield, MI (US)

( * ) Notice: Subject to any disclaimer, the term of this patent is extended or adjusted under 35 U.S.C. 154(b) by 394 days.

(21) Appl. No.: 14/568,438

(22) Filed: Dec. 12, 2014

(65) Prior Publication Data

US 2015/0171602 A1    Jun. 18, 2015

Related U.S. Application Data

(60) Provisional application No. 61/915,088, filed on Dec. 12, 2013, provisional application No. 61/931,131, (Continued)

(51) Int. Cl.
*H01T 23/00*    (2006.01)
*H01T 19/00*    (2006.01)
(Continued)

(52) U.S. Cl.
CPC ............... *H01T 19/00* (2013.01); *F02P 23/04* (2013.01); *G01M 15/02* (2013.01); *G01N 27/02* (2013.01);
(Continued)

(58) Field of Classification Search
CPC ...................................................... H01T 19/00
(Continued)

(56) References Cited

U.S. PATENT DOCUMENTS 4,208,992 A    6/1980  Polo
5,149,940 A    9/1992  Davis et al.
(Continued)

FOREIGN PATENT DOCUMENTS

CN    101351638 A    1/2009
CN    101743395 A    6/2010
(Continued)

OTHER PUBLICATIONS

International Search Report, mailed Mar. 25, 2015 (PCT/US2014/069952).

(Continued)

*Primary Examiner* — Stephen W Jackson
(74) *Attorney, Agent, or Firm* — Robert L. Stearns; Dickinson Wright, PLLC

(57) ABSTRACT

A corona ignition system including a corona igniter, an energy supply, and a frequency detector is provided. The energy supply provides energy to the corona igniter during corona events which are spaced from one another by idle periods, during which no energy is provided to the corona igniter. During the idle periods, the frequency detector obtains the resonant frequency of the corona igniter from at least one of an output voltage and an output current of the energy stored in the corona igniter. The resonant frequency measured during this idle period is dependent only on the corona igniter, and not any other components of the system, and thus is very accurate. The drive frequency of future corona events can then be set based on this accurately measured resonant frequency to achieve a robust corona discharge.

20 Claims, 5 Drawing Sheets

Related U.S. Application Data filed on Jan. 24, 2014, provisional application No. 61/950,991, filed on Mar. 11, 2014, provisional application No. 62/072,530, filed on Oct. 30, 2014, provisional application No. 62/090,096, filed on Dec. 10, 2014.

(51) Int. Cl.

| | | |
|---|---|---|
| *G01M 15/02* | (2006.01) | |
| *G01N 27/02* | (2006.01) | |
| *F02P 23/04* | (2006.01) | |
| *H01T 15/00* | (2006.01) | |
| *H02M 3/00* | (2006.01) | |
| *F02P 3/04* | (2006.01) | |
| *F02P 5/15* | (2006.01) | |
| *F02P 17/00* | (2006.01) | |

(52) U.S. Cl.
CPC .............. *H01T 15/00* (2013.01); *H02M 3/00* (2013.01); *F02N 2300/2011* (2013.01); *F02P 3/0407* (2013.01); *F02P 5/1502* (2013.01); *F02P 17/00* (2013.01)

(58) Field of Classification Search
USPC ........................................................ 361/230
See application file for complete search history.

(56) References Cited

U.S. PATENT DOCUMENTS

| | | | |
|---|---|---|---|
| 5,179,928 A | 1/1993 | Cour et al. | |
| 5,361,737 A | 11/1994 | Smith et al. | |
| 5,513,618 A | 5/1996 | Rich et al. | |
| 5,568,801 A | 10/1996 | Paterson et al. | |
| 6,758,199 B2 | 7/2004 | Masters et al. | |
| 6,883,507 B2 | 4/2005 | Freen | |
| 7,956,543 B2 | 6/2011 | Agneray et al. | |
| 7,974,068 B2 | 7/2011 | Agneray et al. | |
| 8,342,147 B2 | 1/2013 | Nouvel et al. | |
| 8,547,020 B2 | 10/2013 | Barroso et al. | |
| 8,552,651 B2 | 10/2013 | Sugino et al. | |
| 8,567,372 B2 | 10/2013 | Visser et al. | |
| 8,578,902 B2 | 11/2013 | Permuy et al. | |
| 8,760,067 B2* | 6/2014 | Burrows ................. | F02P 23/04 315/209 T |
| 8,800,539 B2 | 8/2014 | Toedter et al. | |
| 8,869,765 B2 | 10/2014 | Braeuchle | |
| 9,294,102 B2* | 3/2016 | Kernwein ............... | F02P 23/04 |
| 9,318,881 B2* | 4/2016 | Burrows ................. | H01T 19/00 |
| 9,441,605 B2* | 9/2016 | Schremmer ............ | F02P 9/002 |
| 2004/0129241 A1 | 7/2004 | Freen | |
| 2009/0122583 A1 | 5/2009 | Gelerter | |
| 2009/0194051 A1 | 8/2009 | Smith et al. | |
| 2009/0229581 A1 | 9/2009 | Ikeda | |
| 2010/0116257 A1 | 5/2010 | Agneray et al. | |
| 2010/0229639 A1 | 9/2010 | Agneray et al. | |
| 2010/0251995 A1 | 10/2010 | Nouvel et al. | |
| 2010/0282198 A1 | 11/2010 | Hampton et al. | |
| 2010/0313841 A1 | 12/2010 | Agneray et al. | |
| 2011/0114071 A1 | 5/2011 | Freen | |
| 2011/0146607 A1 | 6/2011 | Smith et al. | |
| 2011/0175691 A1 | 7/2011 | Smith et al. | |
| 2011/0253114 A1 | 10/2011 | Schremmer | |
| 2011/0297132 A1 | 12/2011 | Schremmer et al. | |
| 2011/0305998 A1 | 12/2011 | Toedter et al. | |
| 2012/0055430 A1 | 3/2012 | Braeuchle | |
| 2012/0055455 A1 | 3/2012 | Ruan et al. | |
| 2012/0063054 A1 | 3/2012 | Burrows et al. | |
| 2012/0145136 A1 | 6/2012 | Burrows et al. | |
| 2012/0180742 A1 | 7/2012 | Burrows | |
| 2012/0249006 A1 | 10/2012 | Burrows | |
| 2012/0249163 A1 | 10/2012 | Burrows | |
| 2013/0208393 A1 | 8/2013 | Hampton et al. | |
| 2013/0300474 A1 | 11/2013 | Chang et al. | |
| 2013/0308347 A1 | 11/2013 | Sato et al. | |
| 2014/0226252 A1 | 8/2014 | Freen | |

FOREIGN PATENT DOCUMENTS

| | | |
|---|---|---|
| CN | 102562412 A | 7/2012 |
| CN | 102804527 A | 11/2012 |
| CN | 103597202 A | 2/2014 |
| DE | 19747701 A1 | 5/1999 |
| DE | 102005036968 A1 | 2/2007 |
| DE | 102010062304 A1 | 6/2012 |
| DE | 102010062305 A1 | 6/2012 |
| WO | 2010011838 A1 | 1/2010 |
| WO | 2012138674 A1 | 10/2012 |

OTHER PUBLICATIONS

International Search Report, mailed Mar. 25, 2015 (PCT/US2014/069947).

International Search Report, mailed Mar. 25, 2015 (PCT/US2014/069958).

International Search Report, mailed Mar. 25, 2015 (PCT/US2014/069974).

* cited by examiner

NON-INVASIVE METHOD FOR RESONANT FREQUENCY DETECTION IN CORONA IGNITION SYSTEMS

CROSS-REFERENCE TO RELATED APPLICATIONS

This U.S. patent application claims the benefit of U.S. provisional patent application No. 61/915,088, filed Dec. 12, 2013; U.S. provisional patent application No. 61/931,131; filed Jan. 24, 2014; U.S. provisional patent application No. 61/950,991, , filed Mar. 11, 2014; U.S. provisional patent application No. 62/072,530, filed Oct. 30, 2014; and U.S. provisional patent application No. 62/090,096; filed Dec. 10, 2014, the entire contents of each being incorporated herein by reference in their entirety.

BACKGROUND OF THE INVENTION

1. Field of the Invention

This invention relates generally to a corona discharge ignition system, and more particularly to controlling energy supplied to the system.

2. Related Art

Corona discharge ignition systems provide an alternating voltage and current, reversing high and low potential electrodes in rapid succession which enhances the formation of corona discharge and minimizes the opportunity for arc formation. The system includes a corona igniter with a central electrode charged to a high radio frequency voltage potential and creating a strong radio frequency electric field in a combustion chamber. The electric field causes a portion of a mixture of fuel and air in the combustion chamber to ionize and begin dielectric breakdown, facilitating combustion of the fuel-air mixture, which is referred to as an ignition event. The electric field is preferably controlled so that the fuel-air mixture maintains dielectric properties and corona discharge occurs, also referred to as a non-thermal plasma. The ionized portion of the fuel-air mixture forms a flame front which then becomes self-sustaining and combusts the remaining portion of the fuel-air mixture. Preferably, the electric field is controlled so that the fuel-air mixture does not lose all dielectric properties, which would create thermal plasma and an electric arc between the electrode and grounded cylinder walls, piston, metal shell, or other portion of the igniter. An example of a corona discharge ignition system is disclosed in U.S. Pat. No. 6,883,507 to Freen.

In addition, the corona discharge ignition system is preferably controlled so that energy is provided to the corona igniter at a drive frequency equal or close to the resonant frequency of the corona igniter. This provides a voltage amplification leading to robust corona discharge in the combustion chamber. Detecting the resonant frequency of the corona igniter is necessary in order to achieve this high level of control. However, accurate detection of the resonant frequency it is difficult to achieve, especially at a wide range of frequencies. Changes in the resonant frequency during operation, for example due to arcing events, also make it difficult to accurately detect the resonant frequency.

SUMMARY OF THE INVENTION

One aspect of the invention provides a method of operating a corona ignition system including improved resonant frequency detection. The method includes providing energy to a corona igniter at a first drive frequency during a first period of time, referred to as a corona event. The method also includes providing energy to the corona igniter at a third drive frequency during a third period of time, also referred to as a corona event. The third period of time is spaced from the first period of time by a second period of time. No energy is provided to the corona igniter during the second period of time, and thus the second period of time is referred to as an idle period. The method further includes obtaining a resonant frequency of the corona igniter from at least one of a first output voltage and a first output current of the corona igniter during the second period of time during which no energy is provided to the corona igniter.

Another aspect of the invention comprises a corona discharge system providing improved resonant frequency detection. The system includes a corona igniter, an energy supply, and a frequency detector. The corona igniter has a resonant frequency, and the corona igniter provides a first output voltage and a first output current. The energy supply provides energy to the corona igniter at a first drive frequency during a first period of time and provides energy to the corona igniter at a third drive frequency during a third period of time spaced from the first period of time by a second period of time during which no energy is provided to the corona igniter. The frequency detector obtains the resonant frequency of the corona igniter from at least one of the first output voltage and the first output current during the second period of time during which no energy is provided to the corona igniter.

By measuring the resonant frequency of the corona igniter during the idle second period of time, when no energy is being provided to the corona igniter, an accurate measurement of the true resonant frequency of the corona igniter is obtained. During this idle period, the resonant frequency measured is dependent only on the corona igniter, and not any other components of the system. This accurate resonant frequency measurement can then be supplied to the corona igniter during the next corona event, for example during the third period of time, to achieve a robust corona discharge. Measuring the resonant frequency during the idle second period of time immediately following the corona event is convenient and makes good use of energy stored in the corona igniter that is otherwise wasted. The resonant frequency can be evaluated and adjusted after each corona event, or evaluated over multiple corona events and then adjusted to further improve accuracy.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION

Figure 1:
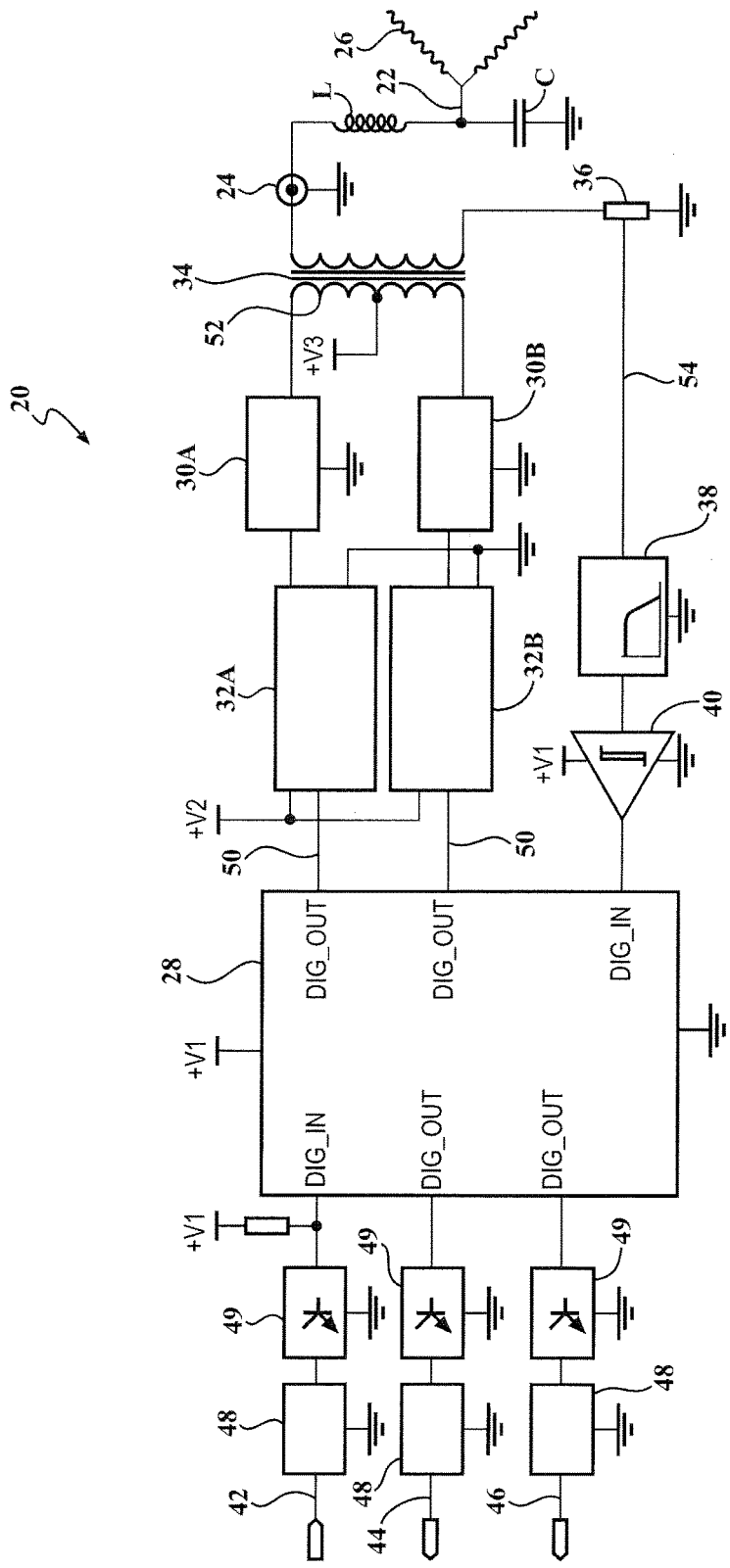
FIG. 1 is a block diagram of a corona discharge ignition system according to a first exemplary embodiment of the invention.

The present invention provides a corona discharge ignition system 20 and method providing improved resonant frequency detection. The system 20 comprises a corona igniter 22 including an induction coil L and capacitor C, together referred to as the load, which operate at a resonant frequency. The corona igniter 22 receives energy at a drive frequency and provides a current and voltage at an input 24. An energy supply V3 provides the energy to the corona igniter 22 at a first drive frequency during a first period of time 101, referred to as a corona event, and during which the corona igniter 22 provides corona discharge 26 in a combustion chamber. The energy supply to the corona igniter 22 is ceased for a second period of time 102, referred to as an idle period, and provided again during a third period of time 103, referred to as another corona event. Some of the energy provided during the first period of time 101 is stored in the corona igniter 22 during the idle second period of time 102. The resonant frequency of this stored energy is dependent only on the corona igniter 22, and not any other components of the system 20, and thus accurately represents the true resonant frequency of the system 20. A frequency detector, for example a current sensor 36 or voltage sensor 78, in combination with a controller 28, obtains the resonant frequency during this idle period. The sensor 36 or 78 typically conveys a signal 54 or 80 including the output voltage or output current, and provides the signal to the controller 28 for analysis. Once the controller 28 identifies the resonant frequency, the control software can be adjusted, preferably during the idle period 102, so that the drive frequency applied during the third period of time 103 matches the accurately measured resonant frequency. The controller 28 can alternatively receive measurements of the resonant frequency from multiple cycles, and then adjust the drive frequency of a subsequent corona event to match an average resonant frequency value obtained from those accurately measured resonant frequencies.

Figure 2:
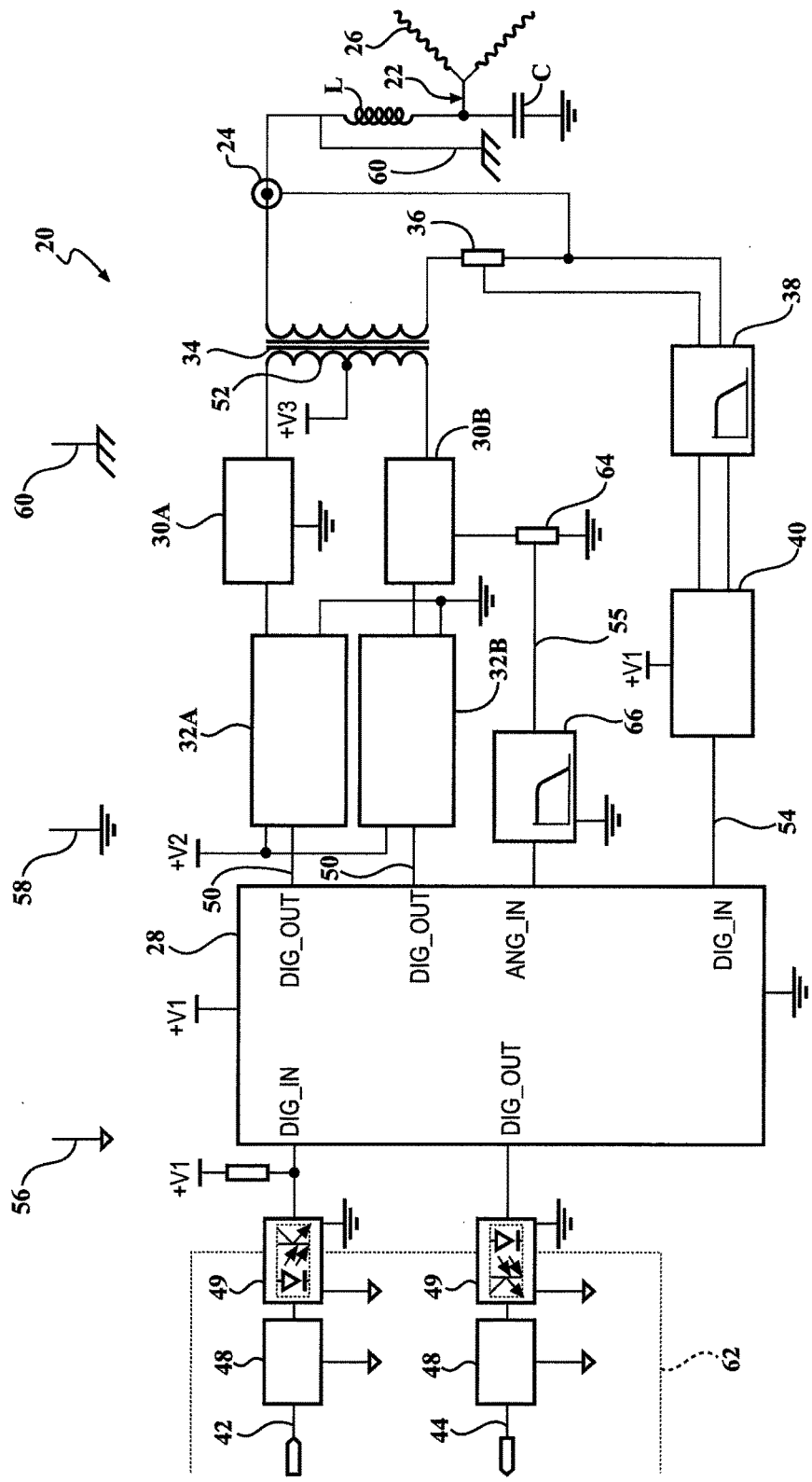
FIG. 2 is a block diagram of a corona discharge ignition system according to a second exemplary embodiment of the invention.
Figure 3:
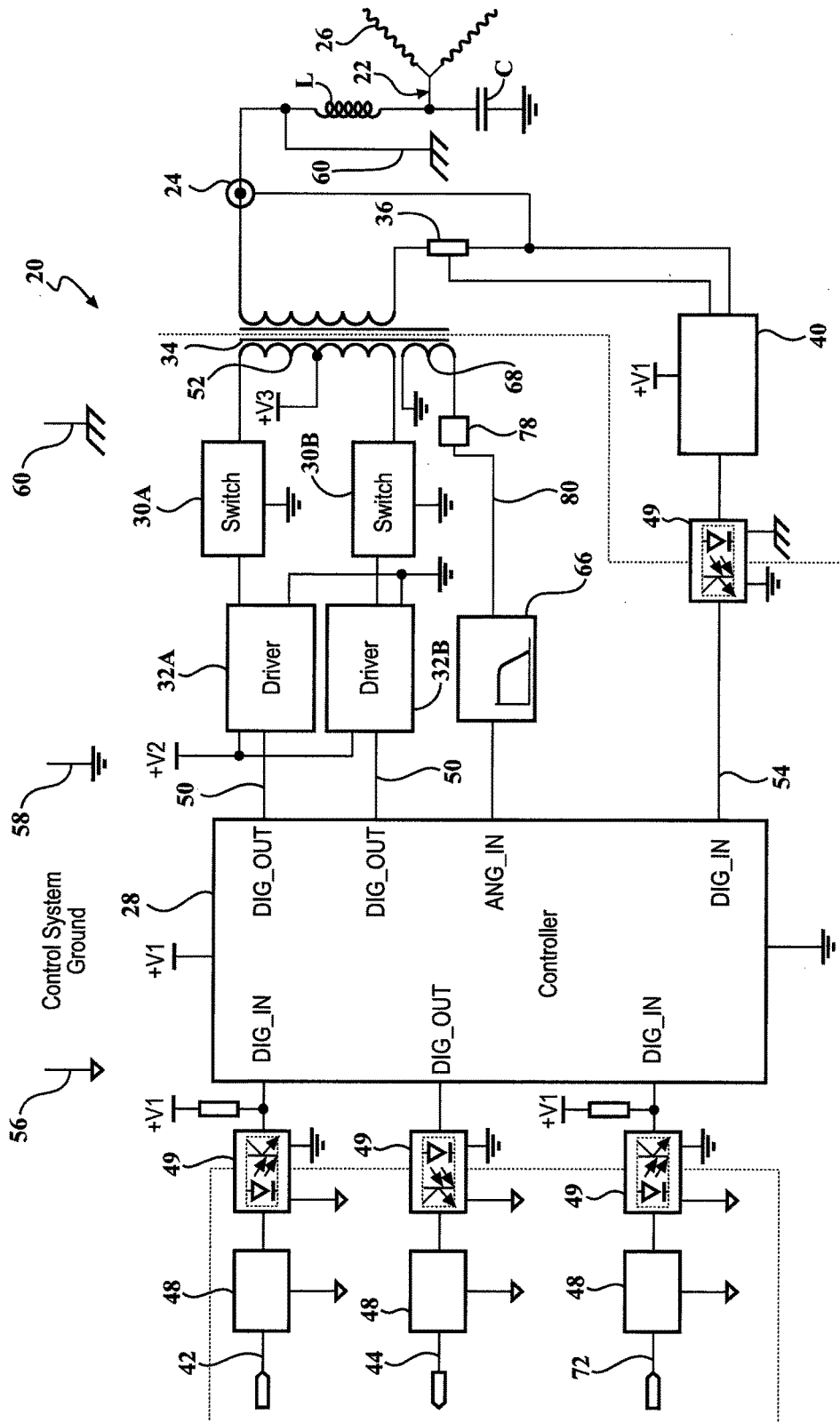
FIG. 3 is a block diagram of a corona discharge ignition system according to a third exemplary embodiment of the invention.

Exemplary embodiments of the corona ignition system 20 providing the improved resonant frequency detection are shown in FIGS. 1-3. These systems 20 are also described in related U.S. patent application Ser. Nos. 14/568,219, 14/568,266, 14/568,330, which are incorporated herein by reference. In each embodiment, the system 20 comprises the corona igniter 22 including the induction coil L coupled to the capacitor C, which are together referred to as the load, operating at a resonant frequency. The corona igniter 22 receives energy at a drive frequency and provides a current and voltage at the input 24 of the corona igniter 22, referred to as an output current and output voltage. During operating in an internal combustion engine, the corona igniter 22 preferably forms a high radio frequency electric field at a firing end, referred to as corona discharge 26, to ignite a mixture of fuel and air in a combustion chamber of the engine. The system 20 also includes the controller 28 and a pair of switches 30A, 30B that control the drive frequency provided to the corona igniter 22, and the capacitance/inductance circuit of the system 20, so that the drive frequency is preferably maintained at the resonant frequency. Operating the system 20 such that the drive frequency is equal to the resonant frequency provides voltage amplification leading to robust corona discharge 26 in the combustion chamber.

The controller 28 of the exemplary embodiments activates one of the switches 30A or 30B at predetermined times to achieve the desired drive frequency. When one of the switches 30A or 30B is active, energy can flow from the power supply V3 through the active switch 30A or 30B to the corona igniter 22. When the switches 30A, 30B are not activated, energy cannot flow through to the corona igniter 22. Although the switch 30A is referred to as the first switch, and the switch 30B is referred to as the second switch, the switch 30B could alternatively be referred to as the first switch, and the switch 30A could be referred to as the second switch. In each case, only one of the switches 30A or 30B is active and providing energy to the corona igniter 22 at any given time during operation of the corona ignition system 20. Thus, the controller 28 deactivates the first switch 30A before activating the second switch 30B, and vice versa, so that the two switches 30A, 30B are not active at the same time. For example, the first switch 30A is active and thus provides energy to the corona igniter 22 whenever the output current is positive, and the second switch 30B is active and thus provides energy to the corona igniter 22 whenever the output current is negative. Preferably, activation of the switches 30A, 30B is synchronized with the resonant frequency of the corona igniter 22.

The system 20 is able to operate at a much wider range of frequencies, compared to other systems. It is also noted that other methods of resonant frequency control which can be employed in the systems described herein are disclosed in related U.S. patent application Ser. Nos. 14/568,219, 14/568,266, 14/568,330, which are incorporated herein by reference. Each application lists the same inventor and was filed on the same day as the present application FIG. 1 is a block diagram of the corona discharge ignition system 20 according to a first exemplary embodiment which is capable of providing and maintaining the drive frequency equal to or approximately equal to the resonant frequency of the corona igniter 22. In addition to the controller 28, switches 30A, 30B, corona igniter 22, the system 20 also includes a pair of drivers 32A, 32B, referred to as a first driver 32A and a second driver 32B. The system 20 of FIG. 1 further includes a transformer 34, a first current sensor 36, a first low-pass filter 38, and a first signal conditioner 40. The output current of the corona igniter 22 is equal to the current at the input 24, which is measured by the first current sensor 36.

The system 20 is controlled by the controller 28, which is preferably a programmable digital or mixed-signal controller, such as a digital signal processor (DSP), complex programmable logic device (CPLD), field-programmable gate array (FPGA), microcontroller, or microprocessor. The controller 28 receives a trigger input signal 42 which commands the controller 28 to initiate the production of corona discharge 26 in the combustion chamber. The controller 28 also provides an arc detect output signal 44 to inform any external control system (not shown) that an arc has been detected, and a feedback output signal 46 to provide additional data about the health and operation of the circuit to any external control system. The trigger input signal 42, arc detect output signal 44, and feedback output signal 46 conveyed to and from the controller 28 are filtered by electromagnetic compatibility filters, referred to as EMC filters 48, and other input filters 49. In response to the trigger input signal 42, the controller 28 provides drive signals 50 to the drivers 32A, 32B which control the switches 30A, 30B. When one of the switches 30A or 30B is active, the energy V3, which is a DC voltage, is applied to a primary winding 52 of the transformer 34. The transformer 34 then provides energy through the input 24 and to the corona igniter 22 at the drive frequency. In the exemplary embodiment, the transformer 34 has a configuration known in the art as a "push-pull" configuration.

In the system 20 of FIG. 1, the current provided from the corona igniter 22 (the output current), is measured at the first current sensor 36 during the idle second period of time 102 using any suitable technique. The first current sensor 36 can be a shunt resistor, hall-effect sensor, or current transformer, for example. A current output signal 54, including a measurement of the output current of the corona igniter 22 during the idle period is conveyed from the first current sensor 36 toward the controller 28. Preferably, this current output signal 54 is lightly filtered by the first low-pass filter 38 before being conveyed to the controller 28. The first low-pass filter 38 creates a phase shift in the current output signal 54 which is smaller than the period of oscillation of the current. In one embodiment, the phase shift is 180 degrees, but preferably the phase shift is less than 180 degrees, and more preferably the phase shift is less than 90 degrees, which is less than one half cycle. The first low-pass filter 38 also removes unwanted high frequency noise generated by switching high current and voltages. The filtered current output signal 54 is then transferred to the first signal conditioner 40, which makes the current output signal 54 safe for transferring to the controller 28. Thus, the current output signal 54 is at a level that can be safely handled by the controller 28. The output current is typically provided to the controller 28 after each corona event, but may be measured for multiple corona events before being provided to the controller 28.

The controller 28 receives the current output signal 54 with the current measurement obtained by the first current sensor 36 during the idle second period of time 102, and uses the current measurement to identify the resonant frequency of the corona igniter 22 and the optimum timing for activating the switches 30A, 30B to give resonant operation. The controller 28 can use various different techniques to identify the resonant frequency of the corona igniter 22 based on the current output signal 54.

In the exemplary embodiment, once the controller 28 determines the timing of the first switch 30A or second switch 30B to be activated, the controller 28 instructs the first driver 32A to activate the first switch 30A or instructs the second driver 32B to activate the second switch 30B. The drivers 32A, 32B are instructed to activate the switches 30A, 30B at the predetermined times, so that the drive frequency of the energy conveyed through the switches 30A, 30B to the transformer 34 and ultimately to the corona igniter 22 is equal to the resonant frequency of the corona igniter 22. In this exemplary embodiment, one of the switches 30A or 30B is activated each time the output current of the corona igniter 22 crosses through zero so that the drive frequency is equal to the resonant frequency of the corona igniter 22.

It is important that only one switch 30A or 30B is active at any given time during operation of the system 20. For example, the controller 28 can activate the first driver 32A which in turn activates the first switch 30A at a time when the output current crosses through zero. Next, the controller 28 turns off the first driver 32A and the first switch 30A, and then activates the second driver 32B, which in turn activates the second switch 30B the next time that the output current crosses through zero. The controller 28 can analyze each current output signal 54 received from the first signal conditioner 40 to accurately detect the resonant frequency, and can adjust the timing of the switches 30A, 30B whenever needed.

FIG. 2 is a block diagram of a corona discharge 26 ignition system 20 according to a second exemplary embodiment of the invention, which operates like the system 20 of FIG. 1, but includes several additional features. One additional feature is that that the various functional sections of the system 20 include a control system ground 56, a power system ground 58, and load ground 60 which are separated from one another. This technique is used to improve EMI and/or electromagnetic compatibility (EMC). The control system ground 56 is isolated from a power system ground 58 by galvanic isolation 62. The transformer 34 isolates the power system ground 58 from the load ground 60, and this isolation must be maintained between the first current sensor 36 and the controller 28. The isolation between the power system ground 58 and the load ground 60 may be achieved by adding galvanic isolation 62 at the first low-pass filter 38 or the first signal conditioner 40. Alternatively, the isolation between the power system ground 58 and the load ground 60 can be achieved by operating the first low-pass filter 38 or the first signal conditioner 40 in a differential mode where only a negligible current can flow through the device. In the system 20 of FIG. 2, only the first signal conditioner 40 operates in differential mode to isolate the power system ground 58 from the load ground 60. One or more of these methods may be employed.

Another additional feature of the system 20 of FIG. 2 is a second current sensor 64 to measure the amplitude of the current in the second switch 30B on the primary side of the transformer 34. The second current sensor 64 specifically measures the current at the output of the second switch 30B. Alternatively, there could be a second current sensor 64 at each of the switches 30A, 30B. The second current sensor 64 provides an additional feedback signal 55 to the controller 28, giving valuable diagnostic information which is not possible through the phase measurement of only the first current sensor 36. For example, it is possible to detect an open or short circuit in the load circuit by measuring the current at the output of the switches 30A, 30B. In addition, the system 20 of FIG. 2 includes a second low-pass filter 66 located between the current sensor and the controller 28 to lightly filter the current output signal 54 before providing the feedback signal 55 to the controller 28.

FIG. 3 is a block diagram of a corona discharge 26 ignition system 20 according to a third exemplary embodiment of the invention. The system 20 of FIG. 3 also includes the galvanic isolation 62, but in this embodiment, the galvanic isolation 62 is located on both the energy input and energy output sides of the controller 28, and completely separates the three grounds 56, 58, 60. One or both of the barriers provided by the galvanic isolation 62 can be omitted if the circuit is designed to operate using fewer grounds.

The system 20 of FIG. 3 further includes another winding, referred to as a voltage feedback winding 68. The voltage provided by the voltage feedback winding 68 reflects the voltage at the input 24 of the corona igniter 22. A voltage sensor 78 is preferably located at the output of the voltage feedback winding 68 to measure this voltage. A voltage output signal 80 including the output voltage is then transferred through the second low-pass filter 66 to the controller 28. The second low-pass filter 66 lightly filters the voltage output signal 80 before providing the voltage output signal 80 to the controller 28. Also, unlike the systems 20 of FIGS. 1 and 2, a control signal 72 is provided to the controller 28 of FIG. 3. The control signal 72 can include any information related to operation of the corona igniter 22, such as whether arcing occurred or the desired voltage.

The features of the exemplary systems 20 shown in FIGS. 1-3, as well as those shown in the related applications, may be used in various combinations, other than those specifically described herein. However, the system 20 should have the ability to drive the corona igniter 22 with an AC signal at or near its resonant frequency; enable and disable this AC drive signal; and measure the frequency of the current or voltage in the corona igniter 22. Specifically, it should be possible to accurately identify the frequency in the minimum number of oscillations, such as less than ten zero crossings, and preferably less than five zero crossings.

Figure 4:
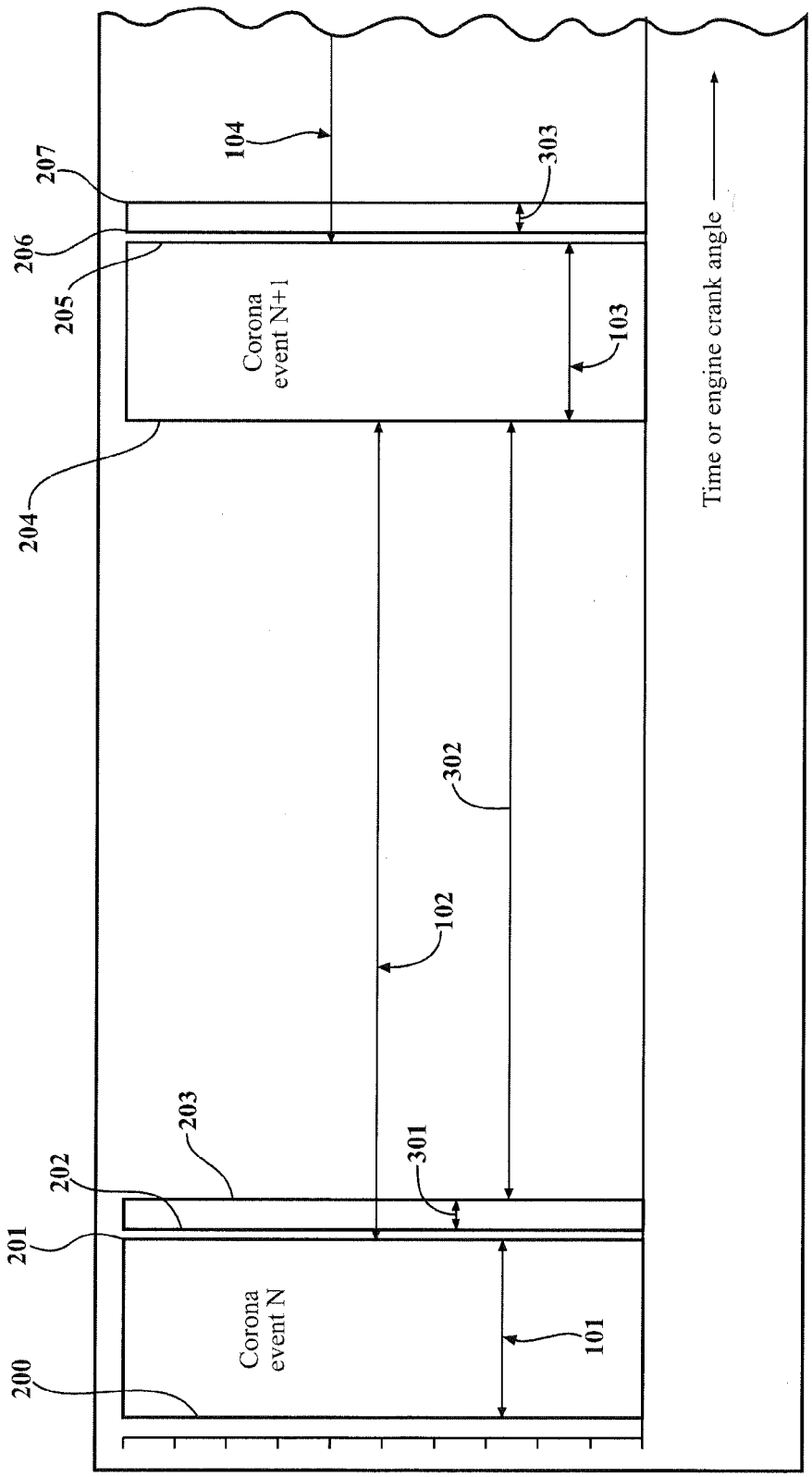
FIG. 4 is a graph illustrating timing of resonant frequency detection relative to timing of energy supply to a corona igniter.

The system of the present invention is capable of implementing the method of accurate resonant frequency detection to achieve exceptional performance, including a robust corona discharge 26. FIG. 4 shows a temporal arrangement, based on time or engine crank angle, of the resonant frequency detection with respect to two corona events 101, 103 for one channel of the system. The channel includes one corona igniter 22, for example as shown in FIGS. 1-3. However, multiple channels may be used, for example in multi-cylinder engine applications, and can be implemented by duplicating the entire system. Alternatively, multiple channels can be implemented by using one system with suitable switching to drive multiple outputs. In each case, the principle of operation is unchanged. During operation of the system, corona discharge 26 is produced in response to one or more control inputs, for example the trigger input signal 42 from an engine control unit, to cause ignition at a required instant.

In FIG. 4, the first corona event, referred to as a first period of time 101, starts when the controller 28, drivers 32A, 32B, and switches 30A, 30B begin to apply energy to the corona igniter at time 200. The first period of time 101 ends when the circuit is disabled at time 201 in response to external inputs to the corona-producing circuit. In the first cycle, when N=1, the resonant frequency has not yet been measured, and thus the system may use a predetermined frequency derived from analysis of the load. This predetermined frequency is typically defined in the software of the controller 28. Alternatively, the system 20 may use a frequency stored in the software of the controller 28 and derived from measurements made during earlier operating periods of the system, if such data is available and has been stored.

At a time 202 which is coincident with or after the ending time of the first corona event 101, the second period of time 102 begins, referred to as an idle period, wherein no energy is provided to the corona igniter 22. During this idle period, there will be some amount of energy stored in the corona igniter 22, or corona circuit, typically in the region of 1 to 25 millijoules. This stored energy is dissipated during a plurality of oscillations of the output voltage and the output current which can be evaluated. Even after the drive circuit providing power is disabled, this energy will continue to circulate between the inductance and capacitance at the resonant frequency of the corona igniter 22 until the energy is dissipated in parasitic losses, such as in the resistance of wires coupled to the corona igniter 22. This stored energy is normally wasted but, in the method of the subject invention, it is evaluated to identify the true resonant frequency of the load.

Specifically, during the second period of time 102, the frequency detector of the system measures and evaluates the output voltage, referred to as a first output voltage, or an output current, referred to as a first output current, of the corona igniter 22 to obtain an accurate measurement of the resonant frequency of the corona igniter 22. In one embodiment, the current sensor 36 or voltage sensor 78 obtains the output current or output voltage, and one of the filters 38 or 66 shifts the signal by not greater than 180 degrees, and more preferably less than 90 degrees, which is less than one half cycle.

As stated above, the resonant frequency obtained during this idle period is dependent only on the load, and not on other components of the system 20. The frequency detector typically includes the controller 28 working in combination with the sensors 36 or 78, or other components of the system 20. According to one exemplary embodiment, the measurement and evaluation of the resonant frequency during the second period of time 102 is done by measuring the interval between successive zero crossings of the output current at the input 24 of the corona igniter 22. Various different techniques can be used to measure the current at the input 24 of the corona igniter 22. For example, the current sensor 36 shown in the systems of FIGS. 1-3 can obtain the output current, and provide a current output signal 54 to the low-pass filter 38 which removes noise from the signal. Alternatively, the voltage sensor 86 shown in FIG. 3 can obtain the output voltage, and provide a voltage output signal 80 to the low-pass filter 66 which removes noise from the signal. The controller 28 then evaluates the zero crossings of the shifted current or voltage signal to identify the true resonant frequency of the system. For example, the controller 28 can measure the interval between successive zero crossings of the output current or output voltage of the corona igniter 22 after the end of the corona event.

Preferably, the resonant frequency is obtained during a first duration of time 301 during the idle period 102, which is immediately after the energy supply to the corona igniter is ceased. FIG. 4 shows this first duration 301 beginning at 202 and ending at 203. This first duration 301 is oftentimes referred to as a measure period. The first duration of time 301 is followed immediately by a second duration of time 302 during which the controller 28 adjusts the control software and changes the stored drive frequency value to match the accurately measured resonant frequency. FIG. 4 shows this second duration beginning at 203 and ending at 204, which is the start of the next corona event. The second duration 302 should be long enough for the resonant frequency to be identified and processed, and long enough for the control software to be updated before the start of the next corona event.

The length of the corona event and idle periods, including the measurement periods, can vary. However, in an exemplary embodiment, the duration of each corona events is typically 20 to 250 microseconds, and the duration of each idle period is typically 15 to 240 milliseconds, with the measurement period being only 5 to 25 microseconds. However, in certain embodiments, where the repetition rate is high or multiple corona outputs must be serviced by one system, the first duration 301 (measurement period) can become shorter, for example less than one millisecond. In this case, the time available to evaluate the resonant frequency can become the limiting factor. In such cases, it may be necessary to evaluate the resonant frequency over a very short period, for example in one resonant cycle or half of one resonant cycle, and use this resonant frequency data to improve the estimate of frequency over many cycles. Of course, where a common circuit drives multiple corona igniters 22, the measured resonant frequencies from different corona igniters 22 need to be kept separate and treated individually.

Figure 5:
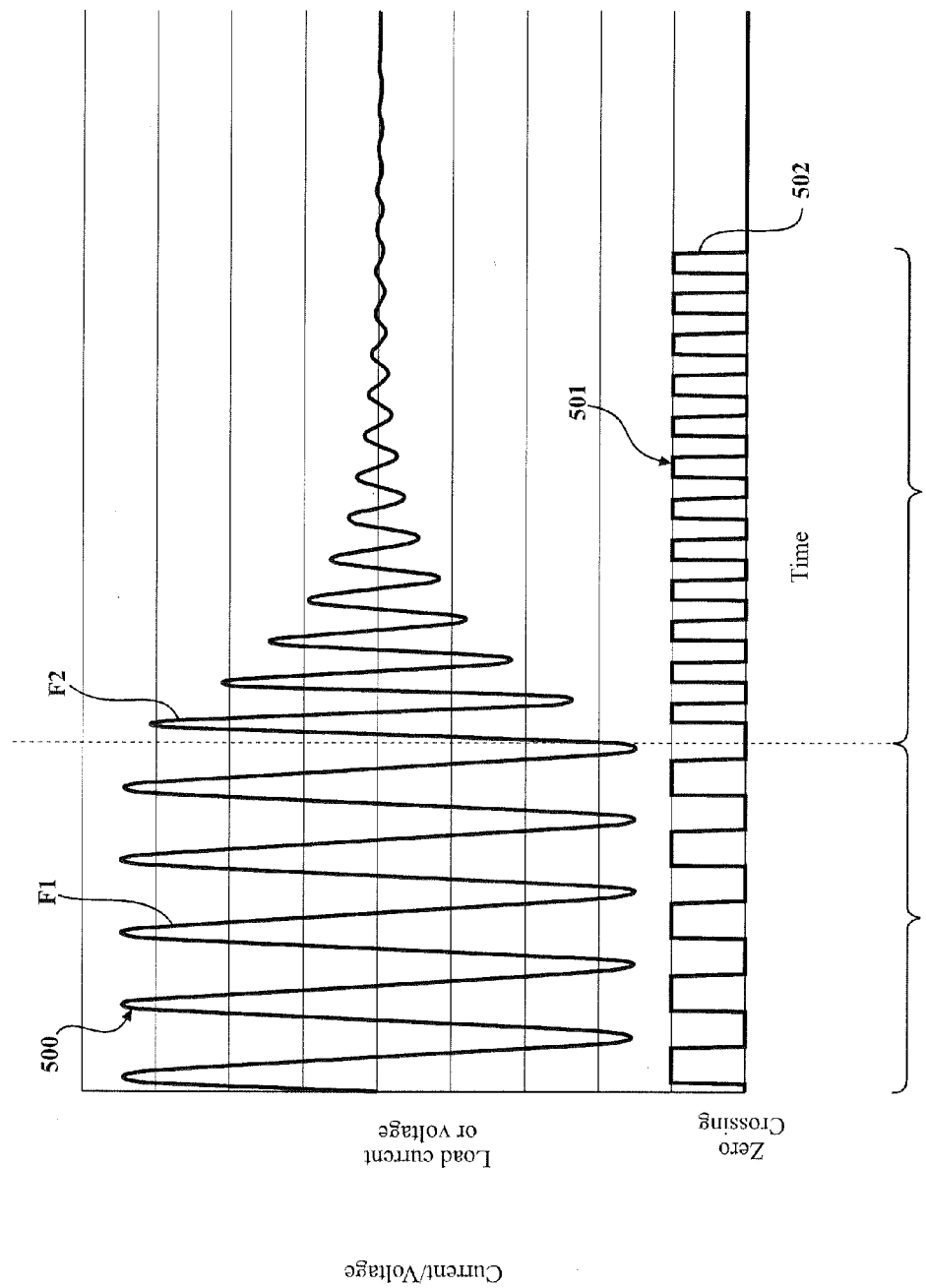
FIG. 5 is a graph illustrating a load current or voltage signal during a corona event when energy is supplied to the corona igniter compared to an idle period when energy is not supplied but remains stored in the corona igniter.

FIG. 5 is an enlarged view of the current or voltage signal at the input 24 of the corona igniter 22 at the end of the first period of time 101 (corona event) followed by the current or voltage signal during the idle second period of time 102, immediately following the first period of time 101, when no energy is being supplied to the corona igniter 22. The portion of the first period of time 101 shown in FIG. 5 is referred to as the corona period 300, and the portion of the idle second period of time shown in FIG. 5 is the measure period 301. During the corona period 300, the load is driven by the controller 28 at a frequency F1, giving a voltage into the load or a current through the load 500 defined by the drive frequency. This current or voltage signal 500 can be derived by any convenient method of several available, such as the techniques described above. The current or voltage signal 500 can also be processed in a number of ways to give a voltage or current signal suitable for analysis by the controller 28, also described above.

In the example shown in FIG. 5, the signal 500 is processed to give a zero crossing signal 501, for example by the low-pass filter 38. There is a slight phase shift between the zero crossing of the signal 500 and the output of the zero crossing 501, which is shifted due to the delay imposed by any filtering or signal conditioning used, and does not affect operation of the system or method. In one embodiment, the phase shift is 180 degrees or less. After the end of the corona period 300 the driving electronics are disabled. However, as discussed above, some energy is stored in the corona igniter 22 during the idle period. The stored energy continues to oscillate between electrical and magnetic during the measure period 301 until it is completely dissipated in the parasitic losses in the load and drive circuits. During this measure period 301 the oscillations have a frequency F2 which is the true resonant frequency of the load. Thus, the controller 28 is designed to evaluate and obtain the resonant frequency during the measure period 301. The length of the measure period 301 can be set such that it is always completed before the end of a lock period 502, where the load signal 500 is too small to be accurately detected.

Alternatively, instead of measuring the frequency F2, the time to make a defined number of transitions or the number of transitions in a defined time could be measured. A "smart" method which could involve counting the total number of transitions and the time taken for them to occur could also be used. Further alternatives include direct analysis of the load signal 500 or frequency domain analysis of either signal, which typically includes FFT analysis. Either the current or voltage signal type can be subject to further processing by the controller 28, such as by application of filtering (analogue or digital), or rejection of zero crossing intervals outside a predefined range or being greatly different from preceding intervals. Other well-known methods of signal processing can also be used. Once the resonant frequency F2 is identified, it can be used either directly as the driving frequency during the next corona period following the measure period 301. The resonant frequency F2 could also be used to improve the accuracy of the estimated drive frequency, for example by averaging the resonant frequency F2 measurements obtained over multiple measure periods 301.

After the accurate resonant frequency measurement is obtained during the idle second period of time 102, the next corona event begins, referred to as the third period of time 103. FIG. 4 shows the third period of time 103 beginning at 204 and ending at 205. Energy is again provided to the corona igniter 22 during the third period of time 103. In one embodiment, the drive frequency provided to the corona igniter 22 during the third period of time 103, referred to as a third drive frequency, is set by the controller 28 so that it is equal to the resonant frequency obtained during the second period of time 102.

After the third period of time 103, the method typically includes another idle period, referred to as a fourth period of time 104, during which no energy is provided to the corona igniter 22. This idle fourth period of time 104 immediately follows the third period of time 103 (corona event), just like the idle second period of time 102 immediately follows the first period of time 101. FIG. 4 shows the fourth period of time 104 beginning at 205, but the end is not shown. This idle period 104 also starts with a measure period 303, beginning at 206 and ending at 207. The duration of the idle fourth period of time 104 can be equal to or different from the duration of the idle second period of time 102. The output voltage and/or output current of the corona igniter 22 during this idle fourth period of time 104, referred to as a second output voltage and a second output current, is measured and evaluated by the frequency detector to obtain the resonant frequency of the load, in the same manner it was obtained during the idle second period of time 102.

Next, the energy supply provides energy to the corona igniter 22 at a fifth drive frequency during a fifth period of time (not shown) spaced from the third period of time by the idle fourth period of time 104. The fifth period of time is referred to as another corona event. The duration of this corona event can be the same as or different from the duration of the previous corona events shown in FIG. 4. During the idle fourth period of time 104, the controller can set the fifth drive frequency so that it equals the resonant frequency measured during the idle fourth period of time 104. In this case, the fifth drive frequency is typically slightly closer to the actual resonant frequency of the load than the third drive frequency.

The cycles of corona events spaced from one another by the idle periods can continue, in the same manner described above. For example, the fifth period of time (corona event) can be followed by an idle sixth period of time during which no energy is provided to the corona igniter 22. The output voltage and current of the corona igniter 22 during this idle period of time is referred to as a third output voltage and a third output current. At least one of the third output voltage and the third output current can be measured at the input 24 of the corona igniter 22 and evaluated by the frequency detector to obtain the resonant frequency of the load during the idle sixth period of time. The control software can again be updated during the idle sixth period of time, in the same manner as it was updated during the idle second and fourth periods of time.

After the idle sixth period of time, the energy supply can provide energy to the corona igniter 22 at a seventh drive frequency during a seventh period of time (not shown). The seventh period of time is another corona event which is spaced from the fifth period of time by the idle sixth period of time. The duration of this corona event can be the same as or different from the duration of the previous corona events. During the idle sixth period of time, the controller 28 can set the seventh drive frequency so that it equals the resonant frequency measured during the idle sixth period of time. In this case, the seventh drive frequency is typically slightly closer to the actual resonant frequency of the load than the fifth drive frequency.

In another embodiment, instead of, or in addition to changing the drive frequency of each the corona event to match the resonant frequency measurement obtained in the immediately preceding idle period, the controller can average the resonant frequency measurements obtained during the second, fourth, and sixth periods of time during which no energy is provided to the corona igniter 22 to obtain an average resonant frequency value; and this average resonant frequency value can be applied to the corona igniter 22 during a future corona event. For example, the energy supply can provide energy to the corona igniter 22 at a ninth drive frequency during a ninth period of time spaced from the seventh period of time by an eighth period of time during which no energy is provided to the corona igniter 22, wherein the ninth drive frequency is equal to the average resonant frequency value provided by the controller 28.

The system 20 and method of the present invention provides multiple advantages over comparative systems. For example, one comparative system attempts to approximate the resonant frequency of the load by making a number of trials at different frequencies and using feedback parameters (e.g. current flow, output voltage, and/or energy consumption), and attempts to identify the closest trial to resonance. Another comparative system adjusts resonant frequency to reduce the phase difference between voltage and current over a significant number of resonant cycles while the driver circuit is energized. Another comparative system measures the phase of the load current during operation and uses this information to directly drive the electronic switches, with the proper phase, so that the system operates at resonance. However, this technique is limited to a certain range of frequencies. The system 20 and method of the present invention, however, allows measurement of the resonant frequency at a time which is normally idle in the operating cycle of the system, and uses energy stored in the corona igniter 22 which is normally wasted. By measuring the resonant frequency while the corona igniter 22 is not powered, the system of the present invention obtains a more accurate measurement of resonant frequency without the need for multiple trials and without the need to introduce extra powered phases in the corona ignition cycle. A complete measurement of the resonant frequency can be made after every corona event, and the measurement can be evaluated and used on a per-cycle basis. Measurement over multiple cycles is not required, but can be done to repeatedly improve the accuracy of the resonant frequency measurement.

Obviously, many modifications and variations of the present invention are possible in light of the above teachings and may be practiced otherwise than as specifically described while within the scope of the claims.

What is claimed is:

1. A method of operating a corona ignition system, comprising the steps of:
   providing energy to a corona igniter at a first drive frequency during a first period of time and at a third drive frequency during a third period of time spaced from the first period of time by a second period of time during which no energy is provided to the corona igniter; and
   obtaining a resonant frequency of the corona igniter from at least one of a first output voltage and a first output current of the corona igniter during the second period of time during which no energy is provided to the corona igniter.

2. The method of claim 1, wherein the third drive frequency is equal to the resonant frequency obtained during the second period of time.

3. The method of claim 2 including adjusting control software during the second period of time so that the energy provided to the corona igniter during the third period of time changes from the first drive frequency to the third drive frequency.

4. The method of claim 2 including providing energy to the corona igniter at a fifth drive frequency during a fifth period of time spaced from the third period of time by a fourth period of time during which no energy is provided to the corona igniter;
   providing energy to the corona igniter at a seventh drive frequency during a seventh period of time spaced from the fifth period of time by a sixth period of time during which no energy is provided to the corona igniter;
   obtaining the resonant frequency of the corona igniter from at least one of a second output voltage and a second output current of the corona igniter during the fourth period of time during which no energy is provided to the corona igniter;
   obtaining the resonant frequency of the corona igniter from at least one of a third output voltage and a third output current of the corona igniter during the sixth period of time during which no energy is provided to the corona igniter; and
   wherein the fifth drive frequency is equal to the resonant frequency obtained during the fourth period of time; and
   the seventh drive frequency is equal to the resonant frequency obtained during the sixth period of time.

5. The method of claim 1, wherein the step of providing energy to the corona igniter is ceased at the second period of time; and wherein the step of obtaining the resonant frequency of the corona igniter is conducted immediately after the energy is ceased.

6. The method of claim 5, wherein the second period of time includes a first duration of time followed by a second duration of time; and including obtaining the resonant frequency only during the first duration; and adjusting control software during the second duration so that the energy provided to the corona igniter changes from the first drive frequency to the third drive frequency.

7. The method of claim 1 including storing a portion of the energy provided to the corona igniter during the first period of time in the corona igniter during the second period of time, and wherein the resonant frequency is obtained from the stored energy.

8. The method of claim 7, wherein the stored energy is between 1 and 25 millijoules and includes a plurality of oscillations of the first output current and the first output voltage, and the resonant frequency is obtained from at least one of the first output current and the first output voltage of the stored energy.

9. The method of claim 1, wherein the step of obtaining the resonant frequency of the corona igniter includes obtaining a signal including the first output current and/or the first output voltage; shifting the signal by not greater than 180 degrees; and evaluating zero crossings of the shifted signal.

10. The method of claim 9 including obtaining the resonant frequency of the corona igniter by measuring an interval between successive zero crossings of the shifted signal.

11. The method of claim 1 including providing energy to the corona igniter at a fifth drive frequency during a fifth period of time spaced from the third period of time by a fourth period of time during which no energy is provided to the corona igniter;
   obtaining the resonant frequency of the corona igniter from at least one of a second output voltage and a second output current of the corona igniter during the fourth period of time during which no energy is provided to the corona igniter;
providing energy to the corona igniter at a seventh drive frequency during a seventh period of time spaced from the fifth period of time by a sixth period of time during which no energy is provided to the corona igniter;
obtaining the resonant frequency of the corona igniter from at least one of a third output voltage and a third output current of the corona igniter during the sixth period of time during which no energy is provided to the corona igniter;
averaging the resonant frequencies obtained during the second, fourth, and sixth periods of time to obtain an average resonant frequency value;
providing energy to the corona igniter at a ninth drive frequency during a ninth period of time spaced from the seventh period of time by an eighth period of time during which no energy is provided to the corona igniter; and
wherein the ninth drive frequency is equal to the average resonant frequency value.

12. A corona ignition system, comprising:
a corona igniter having a resonant frequency, and the corona igniter provides a first output voltage and a first output current;
an energy supply providing energy to the corona igniter at a first drive frequency during a first period of time and providing energy to the corona igniter at a third drive frequency during a third period of time spaced from the first period of time by a second period of time during which no energy is provided to the corona igniter;
a frequency detector obtaining the resonant frequency of the corona igniter from at least one of the first output voltage and the first output current during the second period of time during which no energy is provided to the corona igniter.

13. The system of claim 12, wherein the third drive frequency is equal to the resonant frequency obtained during the second period of time.

14. The system of claim 12, wherein at least a portion of the energy provided to the corona igniter during the first period of time is stored in the corona igniter during the second period of time, and the resonant frequency is obtained from the stored energy.

15. The system of claim 12, wherein the frequency detector includes a controller receiving a signal including the first output current and/or the first output voltage from the corona igniter and determining the resonant frequency from the signal.

16. The system of claim 15, wherein the frequency detector further includes a sensor obtaining the first output current or the first output voltage from an input of the corona igniter; and wherein the sensor conveys the signal including the first output current or the first voltage output the controller.

17. The system of claim 16 including a low-pass filter receiving the signal from the sensor and shifting the signal by not greater than 180 degrees before providing the shifted signal to the controller; and wherein the controller determines the resonant frequency from the shifted signal.

18. The system of claim 15, wherein the controller includes software which is adjusted during the second period of time so that the energy provided to the corona igniter changes from the first drive frequency to the third drive frequency.

19. The system of claim 12, wherein the energy supply includes a power source and a pair of switches providing the energy from the power source to the corona igniter.

20. The system of claim 12, wherein the energy supply provides energy to the corona igniter at a fifth drive frequency during a fifth period of time spaced from the third period of time by a fourth period of time during which no energy is provided to the corona igniter;
the energy supply provides energy to the corona igniter at a seventh drive frequency during a seventh period of time spaced from the fifth period of time by a sixth period of time during which no energy is provided to the corona igniter;
the frequency detector obtains the resonant frequency of the corona igniter from at least one of a second output voltage and a second output current of the corona igniter during the fourth period of time during which no energy is provided to the corona igniter;
the frequency detector obtains the resonant frequency of the corona igniter from at least one of a third output voltage and a third output current of the corona igniter during the sixth period of time during which no energy is provided to the corona igniter;
the controller averages the resonant frequencies obtained during the second, fourth, and sixth periods of time during which no energy is provided to the corona igniter to obtain an average resonant frequency value;
the energy supply provides energy to the corona igniter at a ninth drive frequency during a ninth period of time spaced from the seventh period of time by an eighth period of time during which no energy is provided to the corona igniter; and
the ninth drive frequency is equal to the average resonant frequency value provided by the controller.

* * * * *